United States Patent [19]
Boettger et al.

[11] Patent Number: 4,732,040

[45] Date of Patent: Mar. 22, 1988

[54] ELECTRODYNAMICALLY PRODUCING ULTRASONIC WAVES

[75] Inventors: Wolfgang Boettger, Duesseldorf; Friedhelm Schlawne, Kerpen; Willi Weingarten, Krefeld; Heinz Schneider, Duesseldorf, all of Fed. Rep. of Germany

[73] Assignee: Mannesmann AG, Duesseldorf, Fed. Rep. of Germany

[21] Appl. No.: 807,863

[22] Filed: Dec. 11, 1985

[51] Int. Cl.$^4$ ............................................. G01N 29/04
[52] U.S. Cl. ........................................... 73/643; 73/668
[58] Field of Search .................. 73/643, 622, 637, 638, 73/66 L, 668

[56] References Cited

U.S. PATENT DOCUMENTS

| | | | |
|---|---|---|---|
| 4,232,557 | 11/1980 | Vasile | 73/643 |
| 4,295,214 | 10/1981 | Thompson | 73/643 |
| 4,471,658 | 9/1984 | Morimoto | 73/643 |

FOREIGN PATENT DOCUMENTS 353614  8/1976  U.S.S.R. .................. 73/643

Primary Examiner—Stewart J. Levy
Assistant Examiner—Louis M. Arana
Attorney, Agent, or Firm—Ralf H. Siegemund

[57] ABSTRACT

An electrodynamic transducing device includes two staggerdly coils with a distance of staggering equal to a quarter of a wavelength of ultrasonic waves; unidirectional transmission characteristics of the transducer is obtained by feeding the two coils separately with HF current at a time difference of feeding of the respective two signals to be equal to a quarter of the wavelength such that a reinforcing ultrasonic signal is produced in the direction of the coil receiving said signal earlier in time and complete cancelation of acoustic waves obtains in the opposite direction, whereby in case of equal pitch of said coils the HF signals are of equal contour but of opposite polarity while in case of opposite winding pitch the signals not only have equal signal contour but also the same polarity.

2 Claims, 3 Drawing Figures

ELECTRODYNAMICALLY PRODUCING ULTRASONIC WAVES

BACKGROUND OF THE INVENTION

The present invention relates to an electro-dynamic transducing device for producing ultrasonic waves with a unidirectional characteristics, and including two coils arranged in a lanbda/4 staggered (interdigitized) relationship and in the direction of beaming; these two coils are fed with high frequency currents so that acoustic signals result which interfer in a reinforcing fashion in the direction of beaming but cancel each other (or are supposed to cancel) in the opposite direction.

A transducer of the type to which the invention pertains is, for example, disclosed and described in German Pat. No. 2,655,804, particularly column 8, line 44 et seq. The transducer described a Lamb wave transducer but the present invention refers more broadly also to transducer which may use surface and plate mode oscillations, also tubular wave kind conductor transducers ought to be included.

Transducers generally of the type in which windings receive simultaneously a phase-shifted high frequency signal offers the advantage that, indeed, a large ultrasonic amplitude is produced in the direction of beaming. However, this kind of device is disadvantaged by the fact that the feeding of a hgh frequency signal will produce initially a first acoustic wave by means of the rear coil without concurrent production of an acoustic wave by the front coil in that location of the rear coil so that the cancelling effect in the undersided direction does not obtain. As a consequence a certain parasitic wave is produced which, in turn, may result subsequently in undesired parasitic echo effects.

DESCRIPTION OF THE INVENTION

It is an object of the present invention to provide a new and improved electro-acoustic transducer wherein the cancellation of undesired waves is complete and observable up initio.

In accordance with the preferred embodiment of the present invention it is suggested to feed an hf-current to that one of the coils which is situated first as seen in the direction of the desired beaming, and the other more rearwardly oriented lambda/4 staggered coil receives an hf-powering signal delayed by T/4 whereby, however, the signal shape is the same for both coils, particularly if they are wound with opposite pitch, while an hf-feed signal of similar shape but with opposite polarity is used as the two lambda denotes the wavelength (of the acoustic wave) and T is the oscillation period.

Such a transducer, therefore, will produce an acoustic signal in but one direction, namely in the direction towards that coil which receives the hf-signal earlier than the other one; in other words, the direction of acoustic wave propagation is determined by the timing sequence of feeding current to the two coils. The first in time operating winding produces an acoustic signal which to the extent it propagates opposite to the desired direction will be acoustically cancelled by operation of the somewhat delayedly produced signal in the other (rear) coil. While on the other hand in the direction of desired ultra-sonic wave propagation a maximum amplitude is produced just as described with reference to the device in German Pat. No. 2,655,804, column 8, line 44 et seq. It is, however, important that the feature of the invention is applicable independent of the particular mechanical mode by means of which acoustic waves are produced.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

Proceeding now the the detailed description of the drawings, FIG. 1 illustrates a tube 1 to be inspected and tested with regard to flaws and defects, and for this purpose tube 1 passes progressively through a tubular transducer in the direction of arrow 9. The transducer itself is comprised of a tube or sleeve 2 with external annular grooves denoted by reference numerals 3, 4, 5, and 6. These grooves are spaced apart by a distance equal to one forth of the wavelength of the principal acoustic waves as there will be produced by and in the inventive transducer. The grooves 3, 4, 5, and 6 receive two coils or windings 7 and 8. Herein the winding 8 is first in direction of desired wave propagation, the arrow 9 denotes also the direction of desired wave propagation. The particular coil 8, therefore, has a front winding in groove 4 and is connected to the second coil circular 8 by means of a connection 10, the connection then runs back to groove 6. The second coil 7 being more to the rear vis-a-vis the direction of desired wave propagation, has a front winding which runs in groove 5 and through a connection 11 to groove 3 and back to groove 5. In the particular example, therefore, the two interdigitized coils are wound in hf-generators, not shown in FIG. 1, but explained with reference to FIG. 3, and these hf-generators feed hf-current to the coils.

Figure 1:
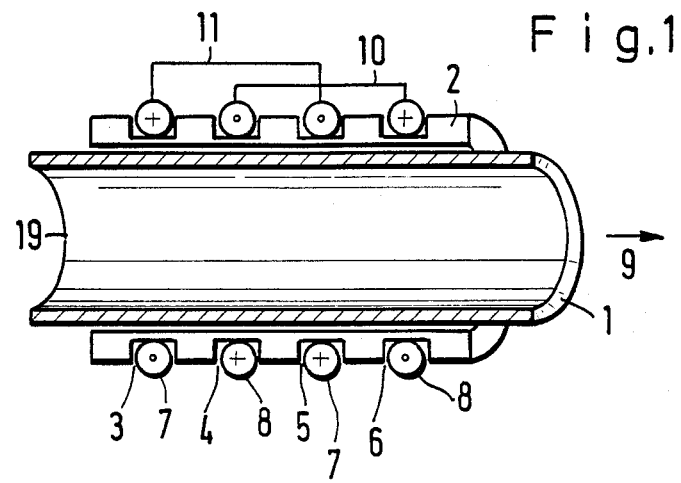
FIG. 1 illustrates a transducer in accordance with the preferred embodiment of the present invention for practicing the best mode thereof in relation to the inspection of tubes with regard to flaws and defects.

Bevore describing the hf-current feed mechanism, the operation of the device in accordance with the invention will be explained with reference to FIG. 2. In accordance with the invention coil 8 receives a feeder hf-current first in time and the time is denoted by t=0, top diagram of FIG. 2. This way two ultra-sonic waves are produced in the tube. These waves are denoted by reference numeral 12 and 13. They are, in fact, in the instant of production one and the same wave, but propagate in opposite directions, i.e. in the desired direction 9 as well as in the opposite direction.

Figure 2:
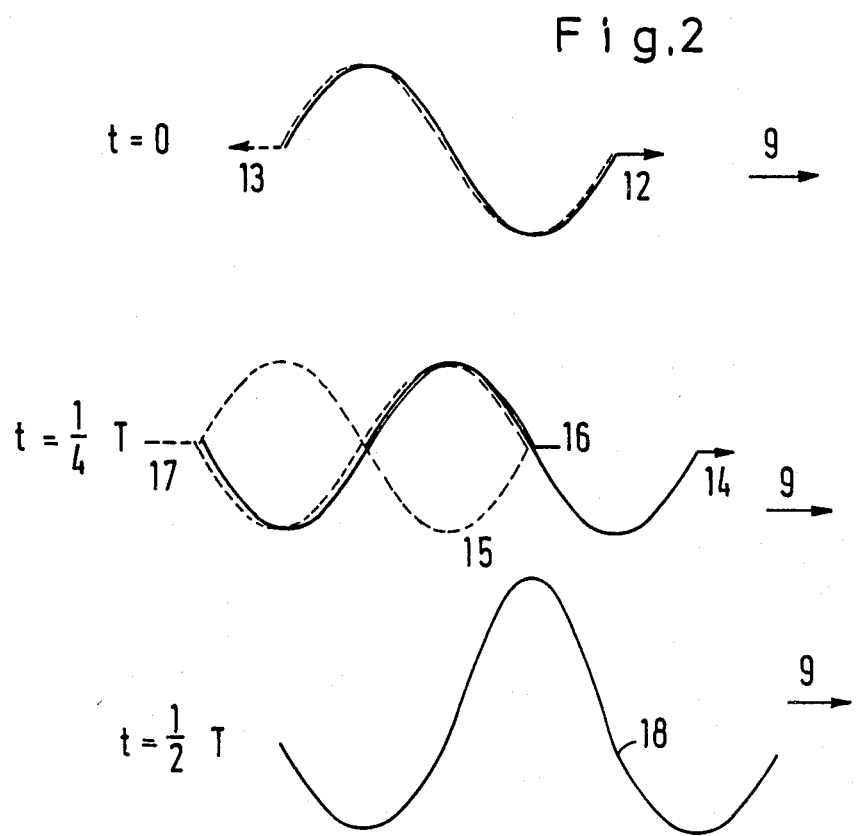
FIG. 2 shows three diagrams of ultra-sonic signals produces and set up in the tubes shown in FIG. 1, and indicating three different points in time as well as a relationship to the axis of the tube in FIG. 1.

At the time t=T/4 wherein T is the oscillation period of the desired ultra-sonic wave, these waves have a contour respectively indicated by reference numerals 14 and 15 in the middle diagram of FIG. 2. One can see that they have propagated by a distance of lambda/4 from the initial point of production to the right and for an equal amount to the left so that, in fact, they are in that instant out of phase by lambda/2. In that instance, i.e. at the instance of t=T/4 coil 7 is fed with an hf-current being delayed in relation to the feeding of hf-current to the coil 8 by T/4. As a consequence two "new" ultra-sonic waves 16 and 17 are produced which also propagate in opposite directions. In fact, of course, these waves are not produced side by side but superimposed so that, in fact, then, a complete wave anihilation occurs in the direction opposite to direction 9. The newly produced wave is superimposed upon 14 so that in fact a wave 12-14 propagates in direction 9 and in a phase reinforcing fashion. The oscillation and ultrasonic wave production in the opposite direction cancel so that, for example, at the end 19 of the tube 1, no reflection of ultra-sonic waves occur. Also, if there are any defects in the tube to the left of the transducer, the defect will likewise not produce any echos. On the other hand, the ultra-sonic wave propagating in the direction 9 has a contour 18 at thetime t=T/2 is shown in the lower diagram of FIG. 2.

It can readily be seen that the principle of the invention can be expanded to include more than two coils and a transducing material in that a plurality of such coils are arranged in the axial direction of the system and the feeding is timed to obtain a progressive build-up of acoustic waves in the desired direction and pairwise cancelation in the opposite direction.

Figure 3:
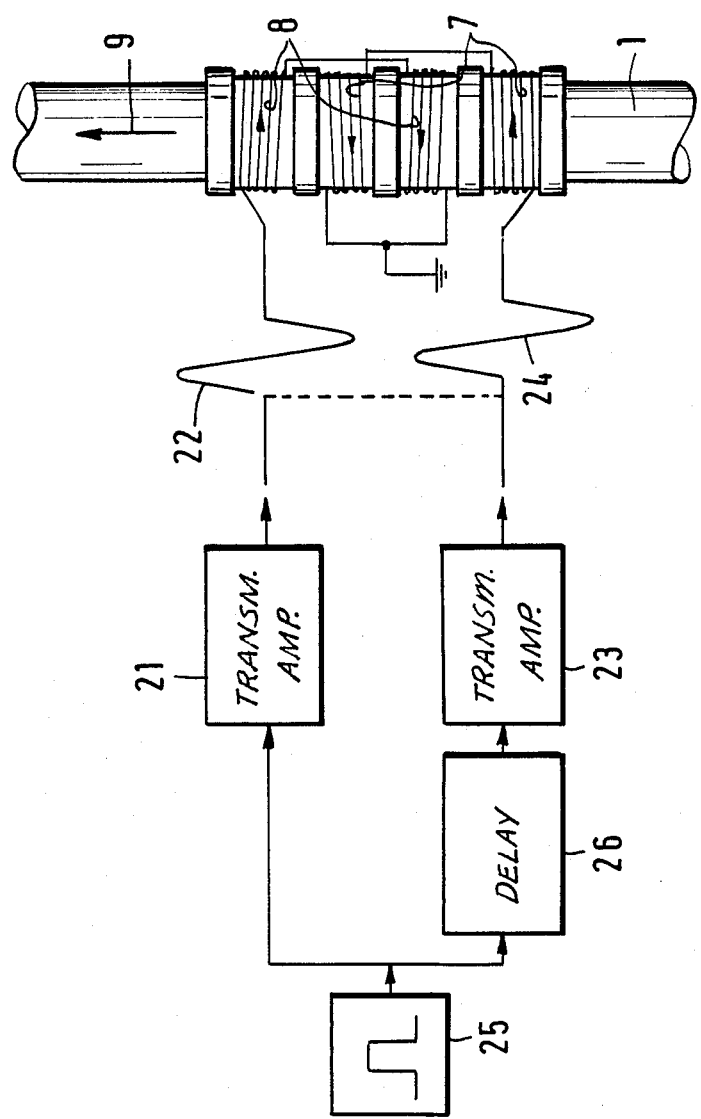
FIG. 3 is a block diagram of electrical equipment for feeding the appropriate signals to the transducer in accordance with the invention.

Turning now to the block diagram of FIG. 3, the tube 1 and the two transducer coil 7 and 8 are shown again together with schematic indication of current feeding. The coil 8 receives a wave signal 22 from a transmitter amplifier 21 and the coil 7 receives a wave signal 24 from the transmitter amplifier 23. As is schematically shown in FIG. 3, these two waves are out of phase by lambda/4. The two amplifiers 21 and 23 are operated from the same signal source such as a pulse source 25, producing directly a sinusoidal or any other suitable wave contour in the transmitter amplifier 21 while the same pulse is fed to the transmitter amplifier 23 but through a delay device 26. 26 is a true delay device so that the pulse shape as it is effective at the input sides 21 and 23 is the same and the two devices 22 and 23 should be of similar construction so that the two waves 22 and 24 have the same contour, amplitude and frequency differing only by lambda/4 in phase.

The invention is not limited to the embodiments described above but all changes and modifications thereof, not constituting departures from the spirit and scope of the invention, are intended to be included.

We claim:

1. Electrodynamic transducing device including two staggerdly coils with a distance of staggering equal to a quarter of a wavelength of ultrasonic waves, the improvement of assuring unidirectional transmission characteristics of said transducer comprising:

means for feeding said two coils separately with discrete HF current pulses and at a particular time difference of feeding of the respective two pulse signals, the time difference being equal to a quarter of the wavelength such that a reinforcing ultrasonic signal is produced in a direction away from the coil receiving said signal earlier in time the coil being displaced in that and complete cancelation of acoustic waves obtains in the opposite direction, whereby in case of equal pitch of said coils the HF signals are of equal contour but of opposite polarity while in case of opposite winding pitch the signals not only have equal signal contour but also the same polarity.

2. A method of operating an electroacoustic transducer which includes at least two spaced but staggerdly arranged coils at an effective spacing of lambda/4 comprising the steps of:

feeding a particular HF signal pulse to one of the coils; and feeding a delayed signal pulse of similar fequency to the otherone of the two coils the delay being equal to a quarter wavelength so that initially reinforcing waves obtain in a first direction and cancelation of waves obtains in the opposite direction.

* * * * *